United States Patent [19]

Wilson, III et al.

[11] Patent Number: 5,101,658

[45] Date of Patent: Apr. 7, 1992

[54] APPARATUS FOR DETERMINING THE THERMAL STABILITY OF FLUIDS

[75] Inventors: George R. Wilson, III; Alf Hundere, both of San Antonio, Tex.

[73] Assignee: Alcor, Inc., San Antonio, Tex.

[21] Appl. No.: 711,120

[22] Filed: Jun. 4, 1991

Related U.S. Application Data

[63] Continuation of Ser. No. 618,117, Nov. 26, 1990, abandoned, which is a continuation of Ser. No. 511,646, Apr. 20, 1990, abandoned.

[51] Int. Cl.[5] .............................................. G01N 33/22
[52] U.S. Cl. ......................................... 73/61.2; 374/43
[58] Field of Search ..................... 73/61.2, 53; 374/43, 374/45; 422/53

[56] References Cited

U.S. PATENT DOCUMENTS

| | | | |
|---|---|---|---|
| 3,141,324 | 6/1960 | Boies | 73/53 |
| 3,229,499 | 1/1966 | Shayeson | |
| 3,318,667 | 5/1967 | Fabuss | |
| 3,529,464 | 9/1970 | Lander | 73/61.2 |
| 3,670,561 | 6/1972 | Hundere | 73/61.2 |

OTHER PUBLICATIONS

ASTM Publ., *Standard Test Method for Thermal Oxidation Stability of Aviation Turbine Fuels*, Dec. 1988.
Lander, Jr., H. R., *Jet Fuel Thermal Stability Test Methods*, in Industry-Military Jet Fuel Quality Symposium-Oct. 22-24, 1968.

*Primary Examiner*—Hezron E. Williams
*Assistant Examiner*—Joseph W. Roskos
*Attorney, Agent, or Firm*—Gunn, Lee & Miller

[57] ABSTRACT

An apparatus for determining the thermal stability of fluids, particularly for testing the deposition characteristics of fuels, comprising a conduit system which connects in series; a reservoir to contain fresh fluid having within it a movable piston capable of discharging the fluid, a heater tube housing in which is mounted a heated tubular member, a time reactor housing of a sufficient volume to decrease the flow of the fluid therethrough, a spent fluid reservoir, a filter located at an outlet of the heater tube housing designed to trap deposits which may be formed due to the heating and remain suspended in the fluid, a similar filter located at an outlet of the time reactor housing designed to trap further deposits that may form with additional time, a differential pressure measuring device connected across each of these filters to measure the pressure drop therethrough, and a valved bypass around each of these filters. The apparatus also contains a water balanced reservoir and pressure regulator whereby the entire system may be maintained at a constant pressure and not discharge volatile organic fuels to the outside.

14 Claims, 4 Drawing Sheets

APPARATUS FOR DETERMINING THE THERMAL STABILITY OF FLUIDS

This is a continuation of copending application Ser. No. 07/618,117 filed on 11/26/90, now abandoned, which is a continuation of application Ser. No. 07/511,646, filed Apr. 20, 1990, now abandoned.

BACKGROUND OF THE INVENTION

1. Field of the invention

This invention relates generally to an apparatus for measuring the thermal characteristics of fluids. Specifically, this invention relates to an apparatus for measuring the thermal oxidation tendencies of fluids, especially fuels used in liquid hydrocarbon burning engines.

2. Description of the Related Art

All major liquid fuel burning engines potentially face the problem of restrictive deposits within the fuel system due to poor fuel thermal oxidative stability. First seen as a problem in fuel systems utilized in gas turbine powered jet aircraft, the problem has now become more widespread and down to earth with the increased use of port fuel injectors in automobile engines.

Every fuel has a temperature above which deposits will begin to form on heated surfaces with which the fuel comes in contact. These deposits may remain on the surface or become suspended in the fuel to be transferred to other parts of the fuel system. The tendency of any fuel to form these deposits is increased by the dissolved oxygen from the air it contacts as well as by various impurities that might exist within the fuel. These deposits result in a number of harmful effects in an engine. Where such deposits occur they have a tendency to reduce the heat transfer properties of the fuel. A more important problem for automobile engines is the tendency of these deposits to clog the all important and often finely calibrated port fuel injectors. The importance of this problem can be seen by the rush in recent years of gasoline marketers to advertise the detergent characteristics of their fuels.

It was recognized early on that it was necessary to have a test device to rate the thermal oxidation characteristics of jet fuels so that their deposit tendencies could be determined prior to use in aircraft. The standards for accomplishing this test have for many years been defined by ASTM method D-3241 which utilizes an apparatus based upon U.S. Pat. No. 3,670,561 (Hundere patent). This application is an improvement upon the Hundere patent and utilizes its basic design as a starting point.

The earlier Hundere patent was designed specifically for testing the deposit characteristics of jet fuels and comprised a single reservoir containing fresh and tested fuels on opposites sides of a movable piston, along with a single heated test vessel, all within a closed test loop. In the Hundere patent fresh fuel was supplied to a test vessel within which a heated tubular member exposed the fuel to a known temperature for a selected period of time. A return line from this heated vessel went through both a cooling system and a constant speed metering pump which maintained the fuel flow within the system and returned the tested fuel to the fuel reservoir. A filter designed to trap deposits which remained suspended in the fuel due to the heating was located at the outlet of the heated vessel, and a differential pressure measuring device was connected across the filter to measure the pressure drop therethrough. By examining this filter and the heated tubular member for any solid deposits, the thermal stability of the fluid could be determined. The apparatus included a pressurized inert gas source whereby the entire system could be kept at a constant pressure in order to maintain an accurate flow across the heated test vessel and to prevent the heated test fuel from boiling.

While the apparatus of the Hundere patent provided a quality standard by which jet fuel could be tested and was widely utilized in the industry, it became questionable as to whether the apparatus could accurately identify the deposits that required high residence times about the heated surface for their formation. Evidence of this problem could be seen in both the apparatus itself and in the real world environment of aircraft and automobile engines. In the real world, it has been changes in the design of aircraft and automobile engines that have created the environment whereby fuels came in contact with heated surfaces for periods of time longer than the Hundere patent was designed to test. Within the apparatus itself, the problem was evidenced by the retention of solids formed only after high resident time periods within the metering pump mechanism. These solids appeared outside those parts of the apparatus where quantitative measurements were normally made.

In addition to the difficulties that the Hundere patent had with long residence times there were a number of characteristics of the apparatus itself that hindered an operator's ability to obtain consistent results.

One problem derived from the method of pumping the test fuel through the test apparatus. In the Hundere patent the circulation of the fuel was controlled by an in line metering pump and was further influenced by the constant pressure supplied by an inert gas source. Because the system pump was in line the fuel flow rate was in part determined by the viscosity of the fuel and in part by the efficiency of the pump. Because the pump was susceptible to contamination from suspended solids in the heated fuel, the flow rate could vary as much as 20% depending upon the extent to which the system pump had become clogged with deposits.

A second difficulty with the Hundere patent involved the necessity of maintaining the test fuel under the constant pressure of an inert gas source. Besides the inconvenience of the ancillary components needed to provide the constant pressure, the system required a mechanism for cutting the pressure when a fuel leak occurred. A preferable alternative would be a system that did not require the constant auxiliary background pressure of the Hundere patent and in general could execute the test under conditions that would allow only small amounts of fuel to escape in the event of a leak.

A third difficulty with the Hundere patent involved the constant attention required of the test operator. A preferable alternative would be a system that provided a greater level of automated test control and monitoring.

SUMMARY OF THE INVENTION

It is therefore an object of the present invention to provide an apparatus for the testing of fluids.

It is another object of the present invention to provide an apparatus for testing the thermal oxidation characteristics of fluids.

It is another object of the present invention to provide an apparatus for measuring the tendency of fluids, particularly fuels, to form deposits when in contact with heated surfaces.

It is another object of the present invention to provide an apparatus for testing the thermal oxidation tendencies of fluids, particularly fuels, which apparatus has a relatively small sample size requirement, is of simple construction, and is easy to operate.

It is another object of the present invention to provide an apparatus for testing the thermal oxidation tendencies of fluids, particularly fuels, which apparatus has a series of stages at which quantitative measurements may be taken of all the deposits that may form within test fuels downstream as a result of thermal oxidation.

It is another object of the present invention to provide an apparatus for testing the thermal oxidation tendencies of fluids, particularly fuels, which apparatus has the capability of testing a broad range of fuels including jet fuels, automobile gasolines, and diesel fuels.

It is another object of the present invention to provide an apparatus for testing the thermal oxidation tendencies of fluids, particularly fuels, which requires a relatively small amount of test fluid and can accurately determine thermal oxidation tendencies through a series of stages and over extended periods of time and thereby facilitate a more accurate prediction of the quality of the fluid and its ability to function under specific conditions.

These and other objects of the present invention will become apparent from the drawings and description given herein and in the appended claims.

DESCRIPTION OF THE PREFERRED EMBODIMENT

Figure 1:
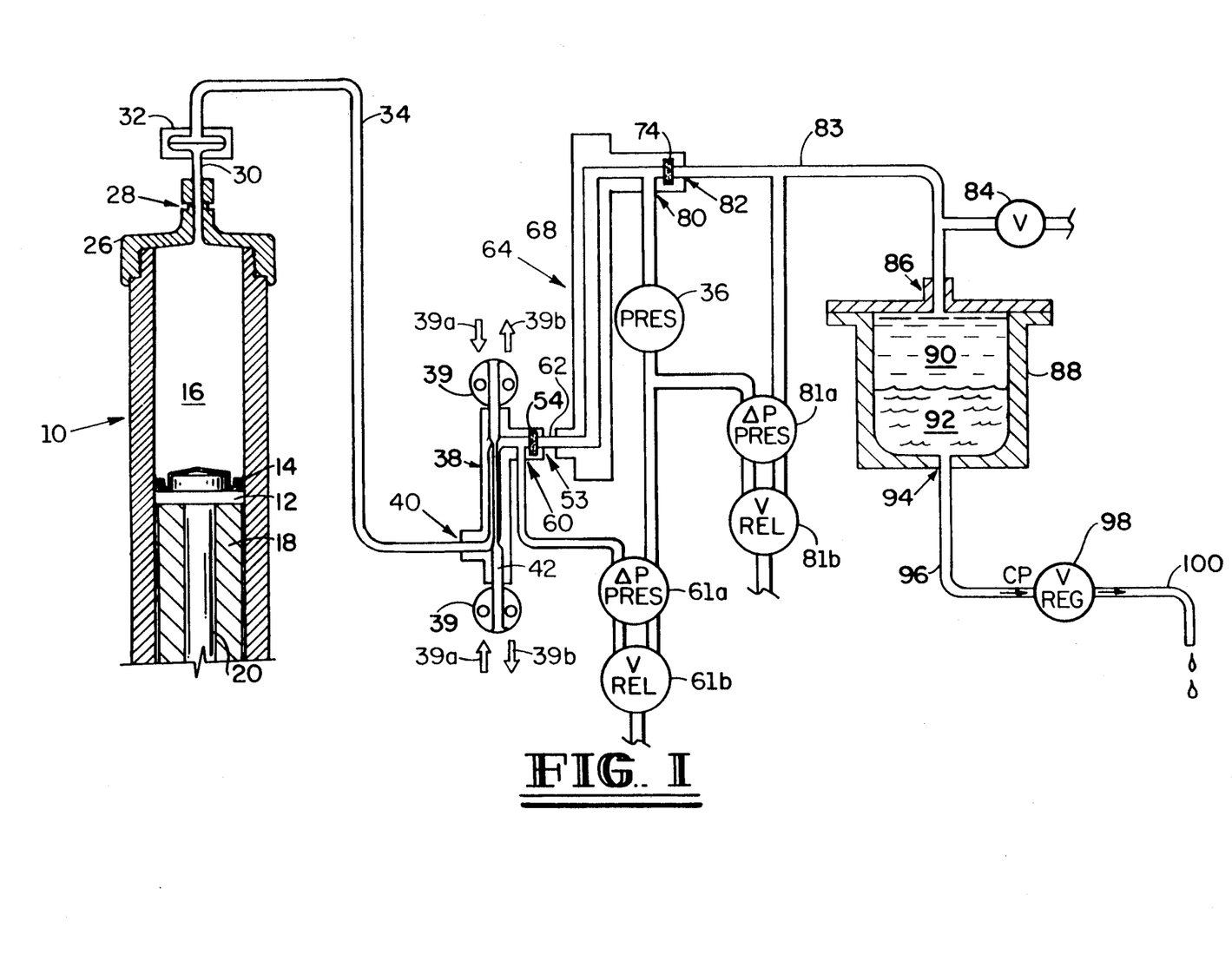
FIG. 1 is a partially schematic diagram of the apparatus of the present invention.

Reference is now made to FIG. 1 for a detailed description of one embodiment of the apparatus of the present invention.

Reservoir 10 is of a generally cylindrical shape and has within it a moveable piston 12 whereby test fuel 16 may be forcibly discharged into the test system. The process of discharging test fuel 16 out of reservoir 10 is described in more detail below with reference to FIG. 3. Fresh test fuel 16 leaves reservoir 10 through conduit 30 and passes through membrane pre-filter 32. Conduit 34 then connects membrane pre-filter 32 to heater tube assembly 38.

Heater tube assembly 38 is equipped with adjacent fluid cooled heater connectors 39 located at each end of heater tube 42. Fluid cooled heater connectors 39 are prevented from overheating themselves by a circulation of coolant fluid through inlet 39a and outlet 39b. The specific components of heater tube assembly 38 are described in more detail below with reference to FIG. 4. Precision filter 54 is located at outlet 53 of heater tube assembly 38 and in front of time reactor assembly 64. A first side of pressure differential monitor 61a is attached at bypass outlet 60 of heater tube assembly 38. This first side of pressure differential monitor 61a is then attached to an inlet of bypass valve 61b.

A short section of conduit 62 connects outlet 53 of heater tube assembly 38 to time reactor assembly 64. The specific components of time reactor assembly 64 are described in more detail below with reference to FIG. 5. A second precision test filter 74 is located at outlet 82 of time reactor assembly 64. Absolute pressure monitor 36 is attached at bypass outlet 80 of time reactor assembly 64. A first side of pressure differential monitor 81a is attached, along with a second side of pressure differential monitor 61a, via absolute pressure monitor 36 to bypass outlet 80. A second side of pressure differential monitor 81a is attached to conduit 83 after time reactor assembly outlet 82. This second side of pressure differential monitor 81a is then attached to an inlet of bypass valve 81b.

Conduit 83 directs fuel 16 away from time reactor assembly 64 to spent fuel reservoir 88. Interrupting conduit 83 is auxiliary bleed valve 84. Within spent fuel reservoir 88 is a sufficient amount of water 92 to offset the quantity of spent fuel 90 arriving from the test system. As spent fuel 90 enters reservoir 88 it displaces water 92 through spent fuel reservoir outlet 94 and thence through conduit 96 in a metered fashion controlled by pressure regulator 98. Water 92 is eventually disposed of via conduit 100. In this manner no spent fuel 90 actually leaves the test system until it is removed as a whole by the removal of spent fuel reservoir 88.

Figure 2:
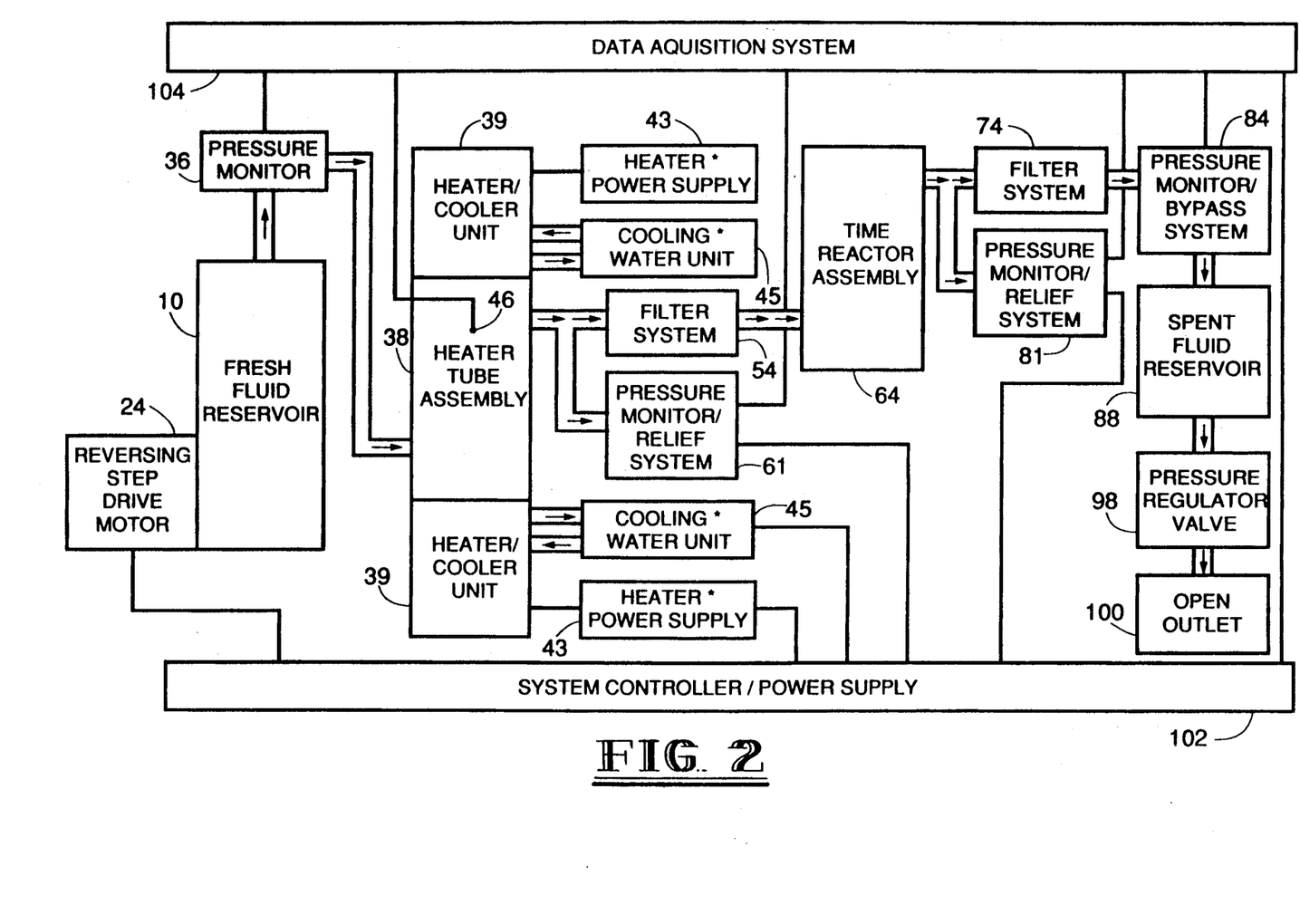
FIG. 2 is a schematic block diagram of the apparatus of the present invention showing the fluid distribution and the electrical control and data acquisition distribution of the present invention.

FIG. 2 is a schematic block diagram of the preferred embodiment shown in FIG. 1 additionally disclosing electrical control and data acquisition connections.

System controller/power supply 102 and data acquisition system 104 are each connected to a number of various components of the test system. System controller/power supply 102 is connected to drive motor 24 and provides both the electrical current and the proportional control signal required by drive motor 24 to incrementally displace test fuel from fresh fluid reservoir 10. Also connected to data acquisition system 104 are pressure monitor/relief systems 61 and 81, and pressure monitor/bypass system 84. Temperature information is received by data acquisition system 104 by way of a connection with thermocouple 46 located within heater tube assembly 38. Data acquisition system 104 provides information to system controller/power supply 102 and is integrally connected thereto for this purpose.

With the information provided by data acquisition system 104, system controller/power supply 102 regulates the power to the fluid cooled heater connectors 39 by way of heater power supply 43. Also with information provided by data acquisition system 104, system controller/power supply 102 controls the relief valve components of pressure monitor/relief systems 61 and 81, and controls the bypass valve component of bypass system 84.

Taken together, system controller/power supply 102 and data acquisition system 104 are designed to free a test operator from constant surveillance and control over the test apparatus.

Figure 3:
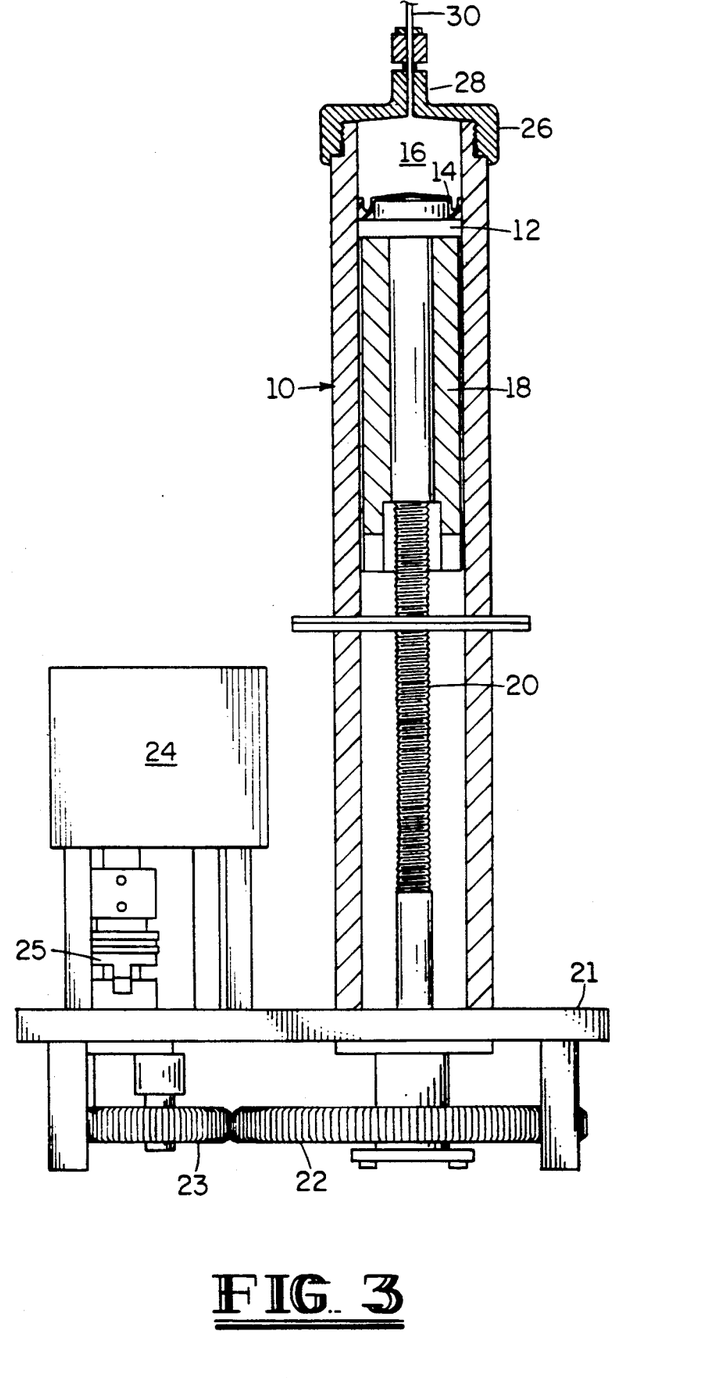
FIG. 3 is a cross-sectional view of the screw drive reservoir.

FIG. 3 is a detailed cross-sectional view of reservoir 10 identified generally in FIG. 1. Fresh test fuel 16 is contained within the reservoir 10. Reservoir 10 is generally of a cylindrical structure within which piston 12 and piston rod 18 are able to move freely. At one end of reservoir 10 is threaded cap 26, which when attached to reservoir 10 makes reservoir 10 substantially airtight except for reservoir outlet 28. Piston 12 is sealed against the interior walls of reservoir 10 by means of a ring gasket 14, and when moved upward against test fuel 16, causes test fuel 16 to exit reservoir 10 through reservoir outlet 28. Piston 12 is pushed from below by piston rod 18 which is attached via threaded section 20 through a cogged belt drive 22 to drive motor 24. By this arrangement piston 12 can be incrementally moved upward to force test fuel 16 from reservoir 10 in graduated amounts. Drive motor 24 is controlled by a reversible DC current that allows the rapid lowering of the piston 12 at the end of one test cycle in preparation for a second test cycle.

Figure 4:
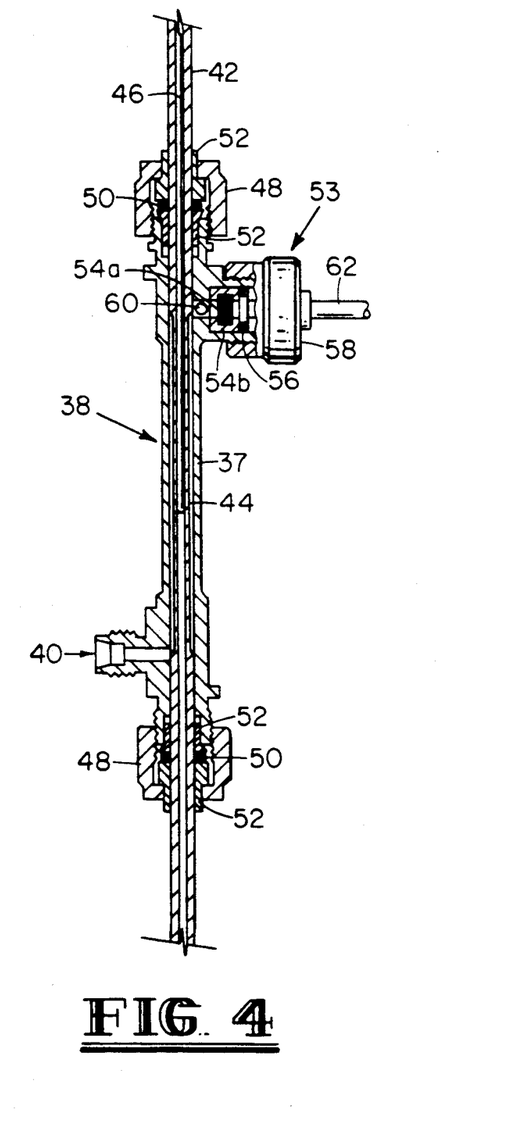
FIG. 4 is a cross-sectional view of the heater tube assembly.

Reference is now made to FIG. 4 for a detailed description of the heater tube assembly 38 shown in FIG. 1. Heater tube assembly 38 is comprised of heater tube housing 37 which has a generally cylindrical bore therethrough and is equipped with inlet 40 and outlet 53. Each end of heater tube housing 37 is equipped with removable cap 48 through which is mounted heater tube 42. In the preferred embodiment heater tube 42 has a substantially constant internal diameter, but has an outside diameter that is larger at the extremities than it is in the central portion. Heater tube 42 is electrically insulated from heater tube housing 37 and removable caps 48 by means of high dielectric insulators 52. Ring seals 50 on each end of heater tube housing 37 prevent leakage of fuel 16 out of heater tube housing 37 around heater tube 42. Thermocouple 46 is mounted inside heater tube 42 to measure the temperature therein. Thermocouple 46 is normally positioned to sense and control the maximum temperature of heater tube 42.

As can be seen from FIG. 4, fuel 16, upon flowing through annulus 44 between the internal walls of heater tube housing 37 and the exterior surface of heater tube 42 passes out of heater tube housing 37 and through heater tube outlet 53. At the heater tube assembly outlet 53 in precision filter 54. Precision filter 54 consists of a piece of precision woven stainless steel cloth 54a held in filter mount 54b. Filter mount 54b and conduit 62 are secured to heater tube housing 37 by means of removable cap 58. Ring seal 56 is used to seal against leakage. Connection to pressure differential monitoring and bypass system 61 is by way of bypass outlet 60. Should precision filter 54 become clogged, fuel 16 bypasses precision filter 54 and flows instead through heater tube assembly bypass outlet 60 as generally described below.

Heater tube 42 is heated by flowing electricity directly therethrough. Fluid cooled heater connectors 39 attached at each end of heater tube 42 provide both the electrical current for heating heater tube 42, and coolant via inlets 39a and outlets 39b for the purpose of protecting the adjoining components of heater tube assembly 38. This method of heating has several advantages in that it leaves the inside of heater tube 42 open so that its entire length may be probed for temperature measurement. It permits a minimum diameter of $\frac{1}{8}$th inch or smaller with very high heat flux, it allows heater tube 42 to be manufactured from any material available in tubing form such as aluminum for lower temperatures and stainless steel or titanium for higher temperatures, and is typically so economical that a new heater tube 42 can be used for each test.

Figure 5:
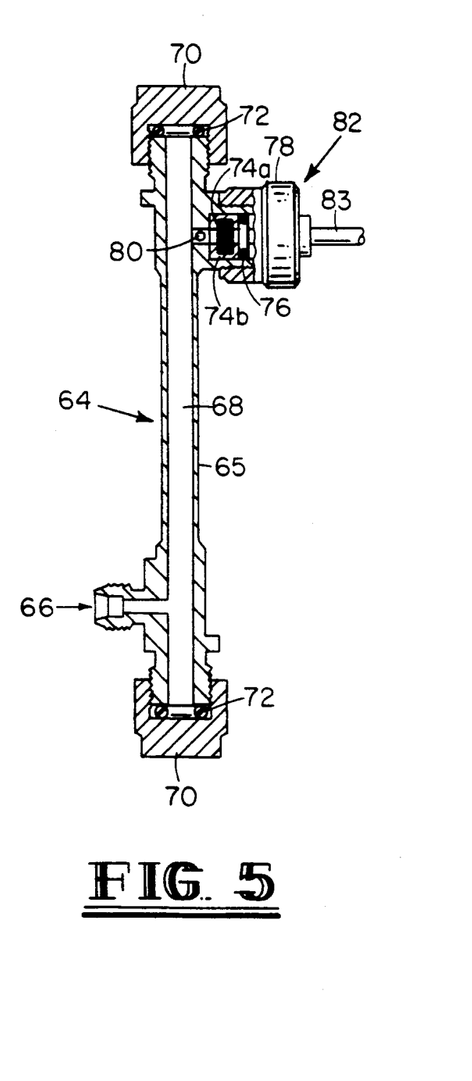
FIG. 5 is a cross-sectional view of the time reactor assembly.

Reference is now made to FIG. 5 for a detailed description of time reactor assembly 64 of FIG. 1. After exiting heater tube assembly 38 by way of conduit 62, test fuel 16 enters time reactor assembly 64 at inlet 66. Time reactor assembly 64 is comprised of time reactor housing 65 capped at either end by removable caps 70. Ring seals 72 prevent fuel 16 from leaking out of time reactor assembly 64. The volume of interior chamber 68 of time reactor assembly 64 controls the residence time of fuel 16 within time reactor assembly 64. The larger the volume of interior chamber 68, the longer the test fuel 16 residence time.

Test fuel 16 exits time reactor assembly 64 at outlet 82 by passing through precision filter 74 and thence to conduit 83. Precision filter 74 consists of a piece of precision woven stainless steel cloth 74a held in filter mount 74b. Filter mount 74b and conduit 83 are secured to time reactor housing 65 by means of removable cap 78. Ring seal 76 prevents the escape of test fuel 16 around removable cap 78. Should precision filter 74 become clogged, fuel 16 bypasses precision filter 74 and instead flows through time reactor assembly bypass outlet 80. Normally test fuel 16 will continue its journey through conduit 83 to spent fuel reservoir 88 as described in FIG. 1.

The method of testing fuel 16 generally follows the path of the test system as it is described above. A test operator begins by removing threaded cap 26 from reservoir 10 and, after determining that piston 12 is in its most downward position, filling reservoir 10 with a measured amount of fresh fuel 16. Fuels that require added oxygen to properly undergo thermal instability reactions are aerated for a few minutes upon being placed in reservoir 10. Threaded cap 26 is then replaced and the system is determined to be ready for testing. Drive motor 24 is activated and incrementally moves piston 12 by way of cogged drive belt 22 and threaded section 20. As piston 12 moves upward through reservoir 10, fuel 16 is forced out of reservoir 10 by way of conduit 30 and through membrane pre-filter 32. Membrane pre-filter 32 insures that any suspended solids that are collected downstream by precision filters 54 and 74 are those formed as a result of the thermal oxidation process and not from existing solids within fuel 16. The grade of pre-filter 32 can be varied to select the purity of the test fuel sample.

From the membrane pre-filter 32 the fuel 16 is forced by the pressure of piston 12 through conduit 34 and into heater tube assembly 38. Absolute pressure monitor 36 allows the operator to monitor the internal pressure of the test system created by piston 12 and the heating that occurs in heater tube assembly 38. Upon entering heater tube assembly 38, fuel 16 is channeled into heater tube housing 37 and around heater tube 42 by way of annulus 44. Heater tube 42 is heated by passing electric current from one end thereof to the other. The temperature of heater tube 42, and thus of test fuel 16, are monitored with thermocouple 46 which has been inserted within heater tube 42. A convenient scheme for electrically heating heater tube 42 that utilizes fluid cooled heater connectors 39 is disclosed in more detail above and in the above mentioned Hundere patent.

The heater tube 42 is generally of circular cross-section and of metallic construction. The type of metal utilized will be dependent upon the operating temperature involved in a specific test. While aluminum is preferred because of the low manufacturing costs, other metals such as stainless steel and titanium may be used if higher temperatures are required or it is desired to duplicate the metal of a specific end application. An important consideration in the manufacture of the heater tube 42 is that of obtaining a surface finish suitable for rating the level of fuel deposits thereon. Normally this requires a highly polished surface that can be accurately maintained with consistency so that deviations from tube to tube will be reduced to a minimum. The deposition level can be either evaluated visually in comparison with a color standard, or by utilizing some other suitable means for sensing the level of deposits.

After contact with heater tube 42, test fuel 16 leaves heater tube housing 37 and passes through precision filter 54. Precision filter 54 is preferably constructed of precision woven stainless steel cloth 54a and has a porosity ranging from five to twenty microns, with seventeen microns being typical. It is preferable that the effective filter diameter of the precision filter 54 be on the order of 0.050-0.150 inches, with 0.100 being typical.

In addition to visual examination of precision filter 54 after completion of the test cycle, the differential pressure across filter 54 can be monitored during the test through pressure differential monitoring and bypass system 61. This system 61 both allows a real time determination of the suspended solid buildup on the filter 54 and a means of bypassing filter 54 if the suspended solid buildup exceeds a given level. Pressure differential monitoring and bypass system 61 is connected to heater tube assembly 38 at bypass outlet 60 and to time reactor assembly 64 at bypass outlet 80.

After exiting heater tube assembly 38, test fuel 16 enters time reactor assembly 64 at inlet 66. Time reactor assembly 64 is comprised primarily of housing 65 which defines interior chamber 68. Time reactor assembly provides a "wide spot" in the test stream that reduces the flow rate of the test fuel 16 and thereby allows a greater time over which post heating thermal oxidation reactions may occur. While there is no additional heating that occurs at the time reactor assembly 64, the housing 65 may be surrounded by a ceramic thermal jacket (not shown) to extend the time at which test fuel 16 remains at high temperature. As mentioned above, the volume of interior chamber 68 determines the residence time of test fuel 16 within time reactor assembly 64. It is therefore preferable to have available a number of different size time reactor assemblies 64 that may be switched out in order to vary the residence time. Alternately, the time reactor assembly 64 may be removed from the test system altogether, and be replaced with an appropriate length of conduit.

At outlet 82 of time reactor assembly 64 is an arrangement essentially identical to that at the outlet 53 of heater tube assembly 38. Precision filter 74, threaded cap 78, and pressure differential monitoring and bypass system 81, all function in much the same manner as their counterparts on the heater tube assembly 38 to provide a means for measuring a degree of solid buildup on precision filter 74 by measuring the pressure differential across precision filter 74.

After exiting time reactor assembly 64 at outlet 82, spent test fuel 90 is carried by conduit 83 to spent fuel reservoir 88. Auxiliary bleed valve 84 allows spent test fuel 90 to be alternately directed away from spent fuel reservoir 88 if the circumstances require.

Spent fuel 90 enters spent fuel reservoir 88 from an inlet 86 so as to dispose spent fuel 90 on the top surface of water 92 within reservoir 88. Spent fuel 90 is controllably allowed to replace water 92 within reservoir 88. Water 92 is allowed to escape reservoir 88 by way of an outlet 94 located at the bottom of reservoir 88. Spent fuel reservoir 88 thus serves not only as a repository for tested fuel 90, but as a final settlement tank for any suspended solid deposits that might have found their way this far downstream. Back pressure on the system is maintained at a controlled level by pressure regulator 98 which permits a metered flow of water 92 out of reservoir 88 through conduits 96 and 100 as the test progresses.

Quantitative data of the thermal oxidative characteristics of a fuel being tested may therefore be gathered from a number of points in the test system. The condition of filters 54 and 74 may be quantitatively measured after removal from the test system and the heater tube 42 may be quantitatively examined as described herein above. A test operator can monitor differential pressures across filters 54 and 74 while the test is in progress, and can examine the final residue formed in spent fuel reservoir 88 after completion of the test cycle. From all of this data an accurate determination of the thermal oxidative characteristics of a given fuel can be obtained.

The method of operation described herein identifies a minimum amount of human interaction because for the most part the various pumping, heating, cooling, and pressure regulating elements may be controlled by an automated, pre-programmed computer device. Such a controller device could be any programmable electronic circuitry capable of sequentially switching on and off a series of output ports appropriately connected to the various elements of the test system. The controller device in the preferred embodiment would also be capable of standard data acquisition functions and would serve to monitor and record the differential pressure variations that are indicative of suspended solid build up, thus alleviating much of the previously required operator attention.

I claim:

1. An apparatus for testing thermal oxidation stability of a fluid such as a hydrocarbon fuel, comprising:

a non-circuitous fluid flow conduit system with an input and an output, said conduit system capable of conducting and containing said fluid;

means for inserting an amount of said fluid into said conduit system at said input of said conduit system;

means for creating and maintaining an incremental flow of said fluid through said conduit system, said incremental flow being maintained at a regulated pressure and being from said input towards said output of said conduit system;

means for controllably heating said fluid in at least one location within said conduit system, said heating means having a surface in contact with said fluid upon which may be deposited suspended solids formed by said heating of said fluid;

means for increasing a total residence time of said fluid within said conduit system at a location between said heating means and said output of said conduit system;

filter means in at least one location within said conduit system between said heating means and said output of said conduit system for trapping said suspended solids formed by said heating of said fluid;

pressure differential measuring means located in conjunction with said filter means for determining a differential pressure across said filter means, said differential pressure being indicative of a degree of said suspended solids deposited on said filter means; and said filter means and said surface of said heating means being so situated within said conduit system as to be monitored for a build up of said suspended solids thereon, said build up of said suspended solids being indicative of said thermal oxidative stability of said fluid.

2. The apparatus claimed in claim 1, wherein said means for creating and maintaining an incremental flow of said fluid through said conduit system comprises:
 a fresh fluid reservoir located at said input of said conduit system, said fresh fluid reservoir having a movable piston therein, said movable piston serving to force said fluid from said fresh fluid reservoir as said piston moves from a first end of said fresh fluid reservoir to an outlet at a second end of said fresh fluid reservoir;
 a spent fluid reservoir located at said output of said conduit system, said spent fluid reservoir containing water, said water capable of being displaced from said spent fluid reservoir by said fluid flowing into said spent fluid reservoir, said spent fluid reservoir having an inlet and an outlet; and
 a pressure regulator valve located at said outlet of said spent fluid reservoir, said pressure regulator valve designed to regulate said displacement of said water from said spent fluid reservoir in a manner which maintains a constant pressure within said apparatus.

3. The apparatus claimed in claim 1, wherein said means for increasing a total residence time of said fluid within said conduit system comprises a time reactor housing having an inlet and an outlet for flowing said fluid therethrough, said time reactor housing having an interior chamber of a size sufficient to reduce said incremental flow of said fluid therethrough.

4. The apparatus claimed in claim 1, wherein at least one of said filter means comprises a precision wire screen placed downstream and proximate to said means for controllably heating said fluid.

5. The apparatus claimed in claim 1, wherein at least one of said filter means comprises a precision wire screen placed downstream and proximate to said means for increasing a total residence time of said fluid within said conduit system.

6. The apparatus claimed in claim 1, wherein said pressure differential measuring means comprises:
 first pressure measuring means located upstream and proximate to said filter means;
 second pressure measuring means located downstream and proximate to said filter means; and
 means for comparing a pressure measured by said first pressure measuring means with a pressure measured by said second pressure measuring means.

7. A method of testing the thermal oxidation stability of a fluid such as a hydrocarbon fuel, comprising the steps of:
 inserting an amount of said fluid into a non-circuitous fluid flow conduit system with an input and an output, said fluid being inserted at said input of said conduit system;
 creating and maintaining an incremental flow of said fluid through said conduit system, said incremental flow being maintained at a regulated pressure and being from said input towards said output of said conduit system;
 controllably heating said fluid in at least one location within said conduit system, said heating occurring at a surface in contact with said fluid upon which may be deposited suspended solids formed by said heating of said fluid;
 increasing a total residence time of said fluid within said conduit system at a location between said location at which said heating occurs and said output of said conduit system;
 filtering said fluid in at least one location within said conduit system between said location at which said heating occurs and said output of said conduit system thereby trapping said suspended solids formed by said heating of said fluid;
 measuring a differential pressure across said location at which said filtering occurs, said differential pressure being indicative of a degree of said suspended solids deposited from said filtering; and
 monitoring said differential pressure, said surface at which said heating occurs, and said location at which said filtering occurs, for a build up of said suspended solids thereon, said build up of said suspended solids being indicative of said thermal oxidative stability of said fluid.

8. An apparatus for testing thermal oxidation stability of a fluid such as a hydrocarbon fuel, comprising:
 a closed reservoir having a movable piston therein, said piston serving to force said fluid from said reservoir as said piston moves from a first end of said reservoir to a second end of said reservoir, said reservoir having an outlet at said second end;
 a heater tube housing having an inlet and an outlet for flowing said fluid therethrough;
 a first conduit means connecting said outlet of said reservoir with said inlet of said heater tube housing;
 a metallic tubular member removably mounted in said heater tube housing with an exterior surface such that said fluid flowing through said heater tube housing passes over said exterior surface of said tubular member, said tubular member having a substantially constant internal diameter, said tubular member further having an outside diameter larger at an upper and a lower extremity than in a central portion thereof;
 means for electrically insulating said tubular member from said heater tube housing;
 means for heating said tubular member by passage of electric current therethrough thereby heating said fluid flowing through said heater tube housing and causing said fluid to partially breakdown chemically, resulting in the formation of suspended solids from said fluid.
 temperature sensing means mounted inside said tubular member;
 first filter means located within said outlet of said heater tube housing for trapping said suspended solids formed by said heating of said fluid in said heater tube housing;
 a spent fluid reservoir containing water, said water capable of being displaced from said spent fluid reservoir by said fluid upon entering said spent fluid reservoir, said spent fluid reservoir having an inlet and an outlet;
 second conduit means connecting said outlet of said heater tube housing to said inlet of said spent fluid reservoir;
 a pressure regulator valve designed to regulate outflow of said water from said spent fluid reservoir in a manner which maintains a constant pressure within said apparatus; and third conduit means connecting said outlet of said spent fluid reservoir with said pressure regulator valve.

9. The apparatus claimed in claim 8, further comprising:
   a time reactor housing insertable between said heater tube housing and said spent fluid reservoir, said time reactor housing having an inlet and an outlet for flowing said fluid therethrough, said time reactor housing having an interior chamber of a size sufficient to reduce a flowrate of said fluid therethrough; and
   second filter means located at said outlet of said time reactor housing for trapping said suspended solids formed from said fluid in said time reactor housing.

10. The apparatus claimed in claim 8, further comprising first differential pressure measuring means located at said outlet of said heater tube housing and across said first filter means so as to measure a pressure drop across said first filter means and thereby indicate a degree of said suspended solids built up on said first filter means.

11. The apparatus claimed in claim 9, further comprising:
    first differential pressure measuring means located at said outlet of said heater tube housing and across said first filter means so as to measure a pressure drop across said first filter means and thereby indicate a degree of said suspended solids built up on said first filter means; and
    second differential pressure measuring means located at said outlet of said time reactor housing and across said second filter means so as to measure a pressure drop across said second filter means and thereby indicate a degree of said suspended solids built up on said second filter means.

12. An apparatus for testing thermal oxidation stability of a fluid such as a hydrocarbon fuel, comprising:
    a closed reservoir having a movable piston therein, said piston serving to force said fluid from said reservoir as said piston moves from a first end of said reservoir to a second end of said reservoir, said reservoir having an outlet at said second end;
    a heater tube housing having an inlet and an outlet for flowing said fluid therethrough;
    first conduit means connecting said outlet of said reservoir with said inlet of said heater tube housing;
    a metallic tubular member removably mounted in said heater tube housing with an exterior surface such that said fluid flowing through said heater tube housing passes over said exterior surface of said tubular member, said tubular member having a substantially constant internal diameter, said tubular further having an outside diameter larger at an upper and at a lower extremity than in a central portion thereof;
    means for electrically insulating said tubular member from said heater tube housing;
    means for heating said tubular member by passage of electric current therethrough and thereby heating said fluid flowing through said heater tube housing and causing said fluid to partially breakdown chemically, resulting in the formation of suspended solids from said fluid;
    temperature sensing means mounted inside said tubular member;
    first filter means located at said outlet of said heater tube housing for trapping said suspended solids formed by said heating of said fluid in said heater tube housing;
    first differential pressure measuring means located at said outlet of said heater tube housing and across said first filter means so as to measure a pressure drop across said first filter means and thereby indicate a degree of said suspended solids built up on said first filter means;
    a time reactor housing having an inlet and an outlet for flowing said fluid therethrough, said time reactor housing having an interior chamber of a size sufficient to reduce a flowrate of said fluid therethrough;
    second conduit means connecting said outlet of said heater tube housing with said inlet of said time reactor housing;
    second filter means located within said outlet of said time reactor housing for trapping said suspended solids formed from said fluid in said time reactor housing;
    second differential pressure measuring means located at said outlet of said time reactor housing and across said second filter means so as to measure a pressure drop across said second filter means and thereby indicate a degree of said suspended solids built up on said second filter means;
    a spent fluid reservoir containing water, said water capable of being displaced from said spent fluid reservoir by said fluid upon entering said spent fluid reservoir, said spent fluid reservoir having an inlet and an outlet;
    third conduit means connecting said outlet of said time reactor housing to said inlet of said spent fluid reservoir;
    a pressure regulator valve designed to regulate outflow of said water from said spent fluid reservoir in a manner which maintains a constant pressure within said apparatus; and
    fourth conduit means connecting said outlet of said spent fluid reservoir with said pressure regulator valve.

13. A method of testing thermal oxidation stability of a fluid such as a hydrocarbon fuel, comprising the steps of:
    storing said fluid in a closed reservoir having a movable piston therein, said piston capable of forcing said fluid from said reservoir as said piston moves from a first end of said reservoir to a second end of said reservoir, said reservoir having an outlet at said second end;
    controllably discharging said fluid from said reservoir by moving said piston from said first end of said reservoir to said second end of said reservoir;
    conducting said fluid from said outlet of said reservoir to a heater tube housing, said heater tube having an inlet and an outlet for flowing said fluid therethrough, said heater tube housing having a metallic tubular member removably mounted therein with an exterior surface, said tubular member having a substantially constant internal diameter, said tubular member further having an outside diameter larger at an upper and a lower extremity than in a central portion thereof;
    conducting said fluid through said heater tube housing thereby placing said fluid in contact with said exterior surface of said metallic tubular member;

controllably heating said fluid by heating said metallic tubular member while in contact with said fluid. thereby forming suspended solids from said fluid;

filtering said fluid of said suspended solids formed as a result of said heating by passing said fluid through a first filter located at said outlet of said heater tube housing;

measuring a differential pressure across said first filter and correlating said differential pressure with a degree of accumulation of said suspended solids on said filter;

conducting said fluid to a spent fluid reservoir containing water, said water capable of being displaced from said spent fluid reservoir by said fluid upon entering said spent fluid reservoir, said spent fluid reservoir having an inlet and an outlet;

displacing said water from said spent fluid reservoir with said fluid by forcing said water from said spent fluid reservoir by way of said outlet;

conducting said water through a pressure regulator valve designed to regulate outflow of said water from said spent fluid reservoir in a manner which maintains constant pressure within said apparatus;

removing said metallic tubular member from said heater tube housing and examining said metallic tubular member for changes in appearance indicative of deposits of said suspended solids thereon;

removing said first filter from said outlet of said heater tube housing and examining said first filter for deposits of said suspended solids thereon; and removing said spent fluid from said spent fluid reservoir and examining said spent fluid reservoir for deposits of said suspended solids therein.

14. The method claimed in claim 13, further comprising the steps of:

conducting said fluid from said heater tube housing to a time reactor housing prior to said step of conducting said fluid to said spent fluid reservoir, said time reactor housing having an inlet and an outlet for flowing said fluid therethrough, said time reactor housing having an interior chamber of a size sufficient to reduce the flowrate of said fluid therethrough;

filtering a second time said fluid of any suspended solids formed as a result of said heating by passing said fluid through a second filter located at said outlet of said time reactor housing;

measuring a second differential pressure across said second filter and correlating said second differential pressure with a degree of accumulation of said suspended solids on said second filter; and removing said second filter from said outlet of said time reactor housing after said step of conducting said fluid to said spent fluid reservoir, and examining said second filter for deposits of said suspended solids thereon.

* * * * *

UNITED STATES PATENT AND TRADEMARK OFFICE
CERTIFICATE OF CORRECTION

PATENT NO. : 5,101,658
DATED : April 7, 1992
INVENTOR(S) : Hundere, Alf and Wilson, George R.

It is certified that error appears in the above-identified patent and that said Letters Patent is hereby corrected as shown below:

On the title page, item [75]:
Inventors: Alf Hundere; George R. Wilson, III, both of San Antonio, Texas Signed and Sealed this Eleventh Day of January, 1994

Attest:

BRUCE LEHMAN

Attesting Officer

Commissioner of Patents and Trademarks